(12) United States Patent
Suga

(10) Patent No.: US 6,478,764 B1
(45) Date of Patent: Nov. 12, 2002

(54) APPLICATOR FOR SANITARY TAMPON

(75) Inventor: Ayami Suga, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 09/534,991

(22) Filed: Mar. 27, 2000

(30) Foreign Application Priority Data

Mar. 31, 1999 (JP) ............................................. 11-092664

(51) Int. Cl.$^7$ ................................................. A61F 13/20
(52) U.S. Cl. ......................................................... 604/15
(58) Field of Search ........................... 604/11–18, 904, 604/311, 285–288

(56) References Cited

U.S. PATENT DOCUMENTS 1,794,221 A * 2/1931 Washburn et al. ............. 604/15
3,628,533 A * 12/1971 Loyer ............................ 604/15
D250,663 S * 12/1978 Koch et al. ..................... 604/15
4,428,370 A * 1/1984 Keely ............................ 604/15

FOREIGN PATENT DOCUMENTS

| JP | 55-155647 | 12/1980 |
| JP | 55-155648 | 12/1980 |

* cited by examiner

Primary Examiner—Dennis Ruhl
(74) Attorney, Agent, or Firm—Lowe Hauptman Gilman & Berner, LLP

(57) ABSTRACT

An applicator for sanitary tampon includes an outer cylindrical tube formed with the maximum outer diameter region. The outer cylindrical tube has its outer diameter gradually increasing rearwardly from its front end until the maximum outer diameter region is reached and then gradually decreasing rearwardly. The maximum outer diameter region extends within ½ of a full length of the outer tube as measured from its front end.

1 Claim, 4 Drawing Sheets

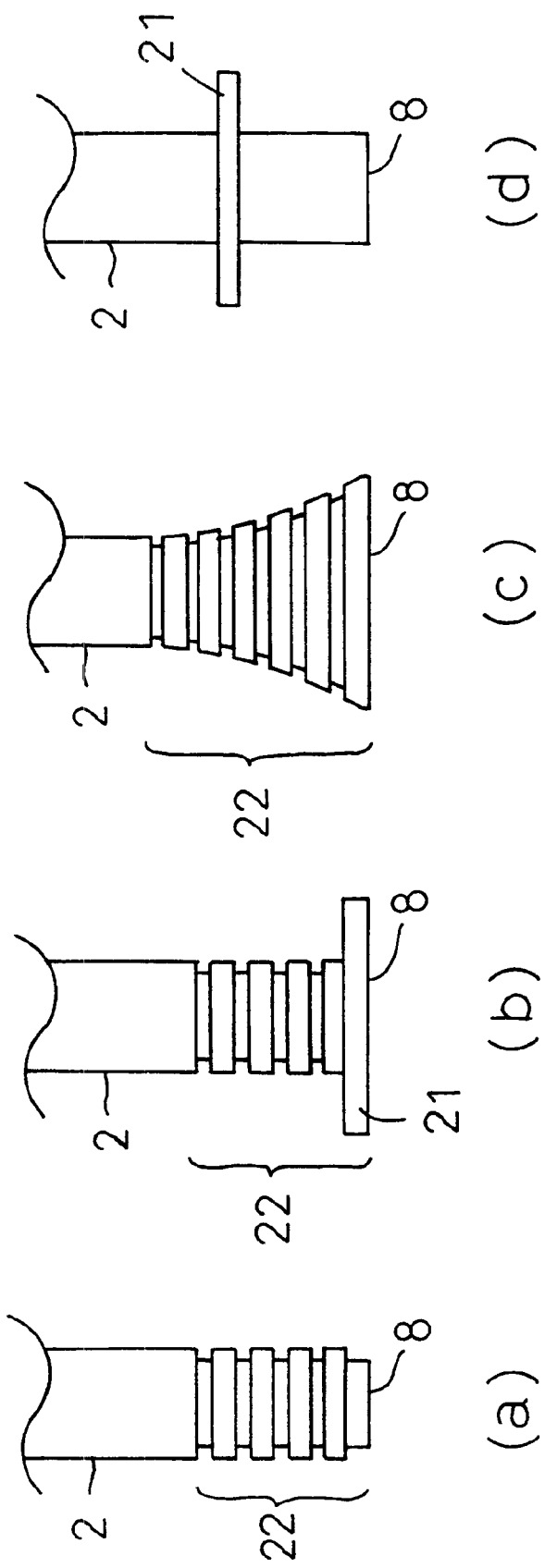

APPLICATOR FOR SANITARY TAMPON

BACKGROUND OF THE INVENTION

This invention relates to an applicator used to insert a sanitary tampon into the vaginal canal of the user.

There has already been proposed an applicator for sanitary tampon, which comprises an outer cylindrical tube and an inner plunger axially movable within the outer cylindrical tube for ejecting a sanitary tampon out of its front end opening into the vaginal canal. It is also well known to provide the outer tube in the form of a cylinder having a substantially uniform outer diameter. Examples of such applicators are described in Japanese Patent Application Disclosure Nos. 1980-155647 and 1980-155648.

The above-mentioned applicators have sometimes encountered the inconvenience such that the applicators are forced back under contraction of sphincteral muscle during introduction of the outer cylindrical tube into the vaginal canal by outstretching the vaginal opening. If such situation occurs in the course of ejecting the tampon out of the outer cylindrical tube, not only the tampon but also the applicator would be no more useful and go to waste. Even if the situation is not so serious, introduction of the outer cylindrical tube into the vaginal canal may sometimes be undesirably delayed.

SUMMARY OF THE INVENTION

It is an object of this invention to provide an applicator enabling a sanitary tampon to be reliably introduced into vaginal canal.

According to this invention, there is provided an applicator for sanitary tampon comprising an outer cylindrical tube having openings at front and rear ends, and an inner plunger axially movable within the outer cylindrical tube for ejecting a sanitary tampon out of the opening at the front end of the outer cylindrical tube into the vaginal canal; and the outer cylindrical tube has an outer diameter thereof gradually increasing rearwardly from the front end until the maximum outer diameter region is reached and then gradually decreasing from behind the maximum outer diameter region wherein the maximum outer diameter region extends within ½ of a full length of the outer cylindrical tube as measured from the front end.

According to one preferred embodiment of this invention, said outer cylindrical tube is formed behind the maximum outer diameter region with the minimum outer diameter region.

According to another preferred embodiment of this invention, the maximum outer diameter of the outer tube is in a range of 8–20 mm and the minimum outer diameter of the outer cylindrical tube is in a range of 20–70% of the maximum outer diameter.

According to still another preferred embodiment of this invention, the outer cylindrical tube is shaped to have, behind the minimum outer diameter region, an outer diameter larger than the minimum outer diameter.

According to further another preferred embodiment of this invention, the inner plunger has, at a front end and/or a rear end thereof, an outer diameter larger than an outer diameter at any intermediate point between the front and rear ends.

According to an additional preferred embodiment of this invention, the inner plunger is provided in the form of tube having openings at a front and rear ends thereof.

According to another additional preferred embodiment of this invention, the outer cylindrical tube is flexible transversely of an axis of said outer cylindrical tube behind the maximum outer diameter region.

BRIEF DESCRIPTION OF THE DRAWINGS

FIG. 4 is a fragmentary diagram of the inner tube, in which (a)~(d) illustrate four specific embodiments thereof.

DETAILED DESCRIPTION OF THE PREFERRED EMBODIMENTS

Details of an applicator for sanitary tampon according to this invention will be more fully understood from the description given hereunder with reference to the accompanying drawings.

Figure 1:
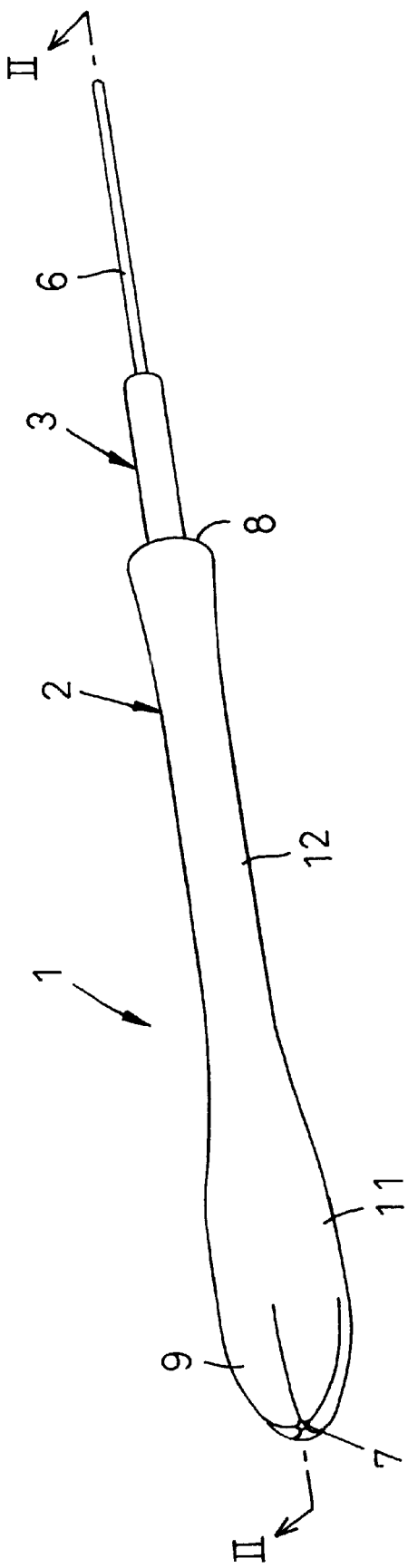
FIG. 1 is a perspective view of an embodiment of the applicator according to this invention.
Figure 2:
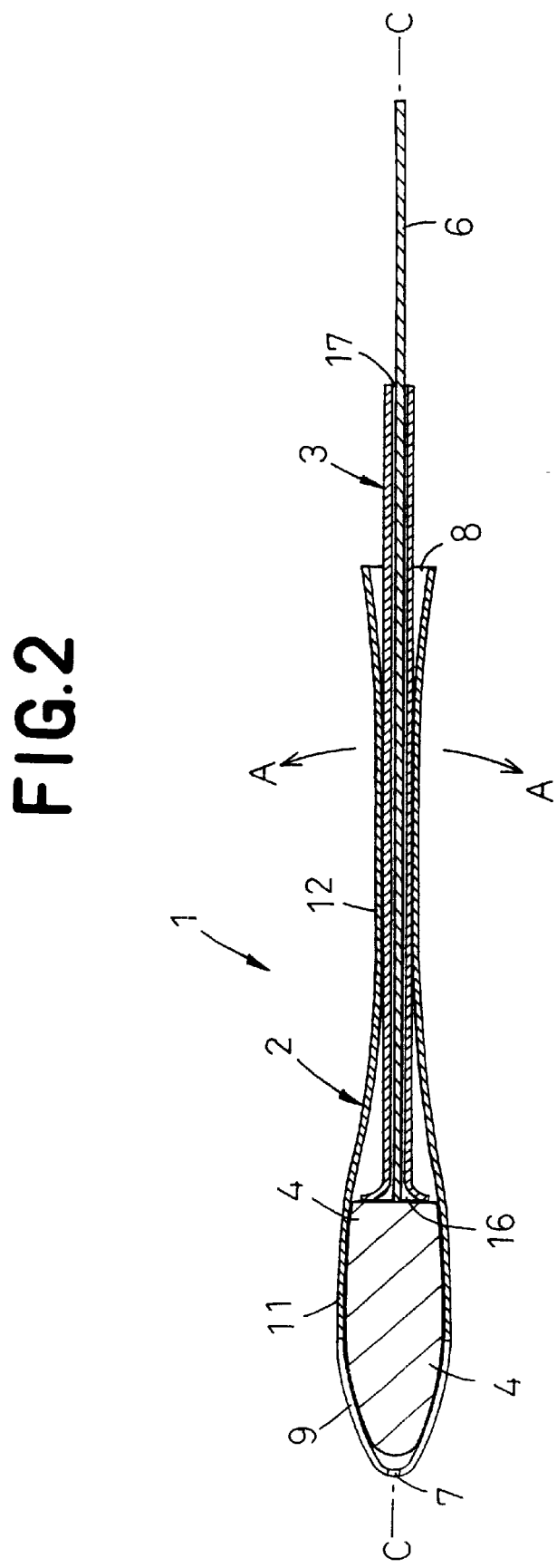
FIG. 2 is a sectional view taken along line II—II in FIG. 1'

FIG. 1 is a perspective view of an applicator and FIG. 2 is a sectional view taken along line II—II in FIG. 1. An applicator 1 comprises an outer cylindrical tube 2, an inner plunger 3, a sanitary tampon 4 cased within the outer cylindrical tube 2 and a string 6 rearwardly extending from a rear end of the tampon 4 through the inner plunger 3 and beyond a rear end of the inner plunger 3. The inner plunger 3 is also in the form of tube.

The outer cylindrical tube 2 has openings 7, 8 at its longitudinally opposite ends, respectively. The front end opening 7 is covered with a plurality of elastically deformable petal-like portions 9 of the outer cylindrical tube 2 and the inner plunger 3 rearwardly extends beyond the rear end opening 8. Between these front and rear end openings 7, 8, the outer cylindrical tube 2 has its outer diameter gradually increasing rearwardly from the front end opening 7 until the maximum outer diameter region 11 is reached. Behind this region 11, the outer diameter gradually decreases until the minimum outer diameter region 12 is reached. Behind this region 12, the outer diameter gradually increases again toward the rear end opening 8.

The maximum outer diameter region 11 extends at most within ½, more preferably in a range of ⅛–½ of a full length of the outer cylindrical tube 2 as measured from its front end. While not specified, the outer diameter of this region 11 may be, for example, in a range of 8~20 mm.

The minimum outer diameter region 12 extends preferably at most in a range of ½ of the full length of the outer cylindrical tube 2 as measured from its rear end. While not specified so far as the inner plunger 3 can be inserted into the outer cylindrical tube 2, the outer diameter of this region 12 is preferably in a range of 20~70% of the outer diameter of the region 11. Behind the minimum outer diameter region 12, the outer cylindrical tube 2 has its outer diameter dimensioned to increase gradually toward its rear end in order to avoid any concern that the applicator might slip off from the user's hand during insertion of the tampon.

A wall thickness of this outer cylindrical tube 2 is substantially uniform and therefore an inner diameter of the outer cylindrical tube 2 varies between its front and rear ends in proportion to a variation of the outer diameter. The front portion of the outer cylindrical tube 2 including the maximum outer diameter region 11 cases therein the tampon 4 and the rear portion of the outer cylindrical tube 2 including the minimum outer diameter region 12 cases the inner plunger 3 extending therethrough.

The inner plunger 3 has a substantially straight configuration and has openings 16, 17 at its front and rear ends. The front end opening 16 has its peripheral edge flaring so that the string 6 of the tampon 4 may be easily inserted into the inner plunger 3 and the rear end of the tampon 4 may be ejected axially forward by the inner plunger 3 over an area as large as possible. The rear end opening 17 of the inner plunger 3 inclusive of a portion in the vicinity of the rear end opening 17 extends outward beyond the rear end opening 8 of the outer cylindrical tube 2.

The tampon 4 is of the well known art in itself wherein the string 6 used to draw out the tampon 4 from the user's vaginal canal extends through the inner plunger 3 and outward beyond the rear end opening 17 of the inner plunger 3. The tampon 4 outstretches the petal-like portions 9 of the outer cylindrical tube 2 until the tampon 4 completely leaves the outer cylindrical tube 2 as the tampon 4 is ejected by the inner plunger 3 from behind.

The outer cylindrical tube 2 is formed by soft and elastic thermoplastic material. Preferably, the rear portion including the minimum outer diameter region 12 is flexible so that the rear portion may be gently curved transversely of an axis C—C of the outer cylindrical tube 2, as indicated by an arrow A. Preferably, the inner plunger 3 also is formed by thermoplastic material and flexible in the direction as indicated by the arrow A. The flexibility of the inner plunger 3 is preferably lower than that of the outer cylindrical tube 2 in order to ensure that the tampon 4 can be smoothly ejected from the outer cylindrical tube 2.

The applicator 1 arranged as has been described above outstretches the sphincteral muscle of the vaginal canal as the applicator 1 is introduced into the vaginal canal. As soon as the maximum outer diameter region 11 has passed the sphincteral muscle, the sphincteral muscle contracts and thereby prevents the applicator being introduced into the vaginal canal from being pushed back therefrom. Accordingly, the applicator 1 of this invention eliminates any concern that the user might fail to introduce the applicator into the vaginal canal as the known applicator has been the case. Once the applicator 1 has been introduced in this manner, the inner plunger 3 may be pushed forward until the tampon 4 is transferred from the outer cylindrical tube 2 into the vaginal canal and received in the inner most region of the vaginal canal. Thereupon the vaginal opening is free from any concern by the tampon 4 and the user is not given any sense of incompatibility. The applicator 1 may have its rear portion which is flexible to be gently curved in the direction as indicated by the arrow A. With such applicator 1, operation of insertion into as well as evulsion from the vaginal canal can be smoothly carried out since the applicator 1 is deformable in conformity with an inner shape of the vaginal canal. The applicator 1 has a substantially straight configuration and the vaginal canal has a curved configuration between the opening and the innermost region of the vaginal canal. As a result, the rear end region of the applicator 1 introduced into the vaginal canal may often partially press the vaginal wall in the vicinity of the vaginal opening and even cause pain to the user. Even in such situation, a degree of the partial pressure exerted on the vaginal wall in the vicinity of the vaginal opening can be minimized, according to this invention, by configuring the rear end region of the outer cylindrical tube 2 to have a small diameter over a relatively long range. In this manner, the above-mentioned inconvenience can be avoided and this inconvenience can be effectively avoided particularly when the outer cylindrical tube 2 is configured to be considerably long.

Figure 3:
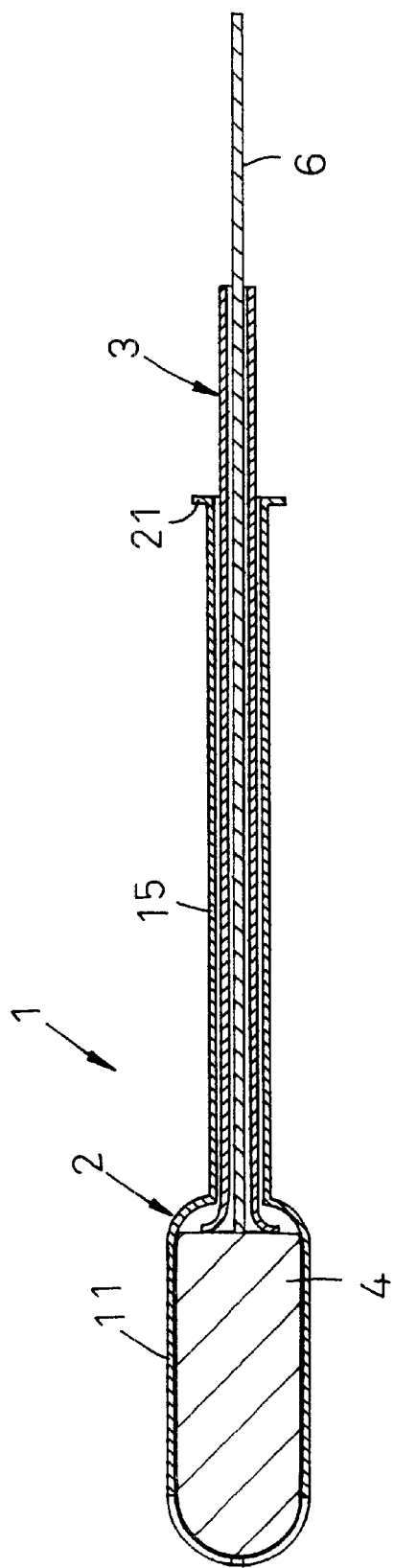
FIG. 3 is a view similar to FIG. 2 depicting another embodiment of the applicator according to this invention.

FIG. 3 is a view similar to FIG. 2 showing another embodiment of this invention. According to this embodiment, the outer cylindrical tube 2 of the applicator 1 has its outer diameter gradually increasing rearwardly from the front end until the maximum outer diameter region 11 is reached. This maximum outer diameter region 11 is followed by a region 15 having a substantially uniform outer diameter. With such applicator 1, variation of its outer diameter before and behind the maximum outer diameter region 11 is sharper than in the case of FIG. 2. The rear end opening 8 of the outer cylindrical tube 2 is formed around its peripheral edge with a flange 21 so that the user may place her finger tips on this flange 21 to push forward the inner plunger 3. However, it should be understood that this flange 21 is not essential to the applicator 1 and can be eliminated without departing from the scope of this invention. The tampon 4 may be replaced by a solid rod-like member if it is unnecessary to insert the string 6 into the tampon 4.

FIG. 4 is a fragmentary diagram illustrating a portion of the outer cylindrical tube 2 in the vicinity of its rear end opening 8. As has already been described, the outer cylindrical tube 2 may be dimensioned to have a relatively large outer diameter in the vicinity of the opening 8 as shown in FIG. 2 or the peripheral edge of the opening 8 may be formed with the flange 21 as shown in FIG. 4 to achieve the convenience of holding the outer cylindrical tube 2 in the course of pushing forward the tampon 4 by the inner plunger 3. This convenience can be achieved also by forming the outer peripheral surface of the outer cylindrical tube 2 with a plurality of slip-preventing steps 22 as illustrated by (a)~(c). Alternatively, the flange 21 may be formed around the outer cylindrical tube 2 ahead of the rear end opening 8, as illustrated by (d) of FIG. 4. These measures are effective also for the inner plunger 3. Specifically, the convenience for holding the inner plunger 3 in the vicinity of its rear end opening 17 may be achieved by dimensioning the outer diameter of the inner plunger 3 to be relatively large in the vicinity of the rear end opening 17 or by forming the inner plunger 3 around its peripheral surface with the slip-preventing steps, as illustrated by (a)~(c).

With the applicator according to this invention, the outer cylindrical tube has its outer diameter gradually increasing rearwardly from the front end until the maximum outer diameter region is reached and decreasing again behind this region. Accordingly, as soon as the maximum outer diameter region has passed the sphincteral muscle of the vaginal opening into the vaginal canal, it is not concerned that the applicator might be pushed back from the vaginal canal. Once the maximum outer diameter region has passed the sphincteral muscle, a pressure possibly exerted on the sphincteral muscle is limited to a pressure by the portion of the outer cylindrical tube having a relatively small diameter. Consequently, the applicator can be easily introduced in the vaginal canal without any significant resistance. The tampon transferred by such applicator into the vaginal canal can be reliably received in the innermost region of the vaginal canal without a possibility that a significant pressure might be exerted upon the vaginal opening and give the user a sense of incompatibility.

What is claimed is:

1. An applicator for sanitary tampon, comprising:
   an outer tube having openings at front and rear ends thereof;
   a sanitary tampon placed in the outer tube; and
   an inner plunger movable in an axial direction within said outer tube for ejecting the sanitary tampon out of said opening at said front end of said outer tube into a vaginal canal;

said outer tube having an outer diameter gradually increasing rearwardly from said front end until a maximum outer diameter region is reached and then gradually decreasing rearwardly from said maximum outer diameter region, wherein said maximum outer diameter region extends between said front end and a midpoint of said outer tube, and has a length of no longer than ½ of a full length of said outer tube;

wherein said inner plunger is formed as an inner tube having openings at front and rear ends thereof.

* * * * *